United States Patent [19]
Mandeville et al.

[11] Patent Number: 6,031,071
[45] Date of Patent: *Feb. 29, 2000

[54] METHODS OF GENERATING NOVEL PEPTIDES

[75] Inventors: Rosemonde Mandeville, Ste. Thérèse; Mikhail Popkov, St. Laurent, both of Canada

[73] Assignee: Biophage, Inc., Montreal, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/590,897

[22] Filed: Jan. 24, 1996

[51] Int. Cl.$^7$ .......................... A61K 38/00; A61K 38/04; C12N 15/00

[52] U.S. Cl. .......................... 530/300; 530/317; 530/324; 530/328; 530/330; 435/252.3; 435/320.1; 536/23.1; 536/23.5

[58] Field of Search .............................. 435/5, 69.1, 69.3, 435/69.7, 239, 320.1, 252.3; 436/543, 802; 530/300, 328, 344, 330, 317, 327, 324; 935/80; 536/23.5, 23.1

[56] References Cited

U.S. PATENT DOCUMENTS

| | | | |
|---|---|---|---|
| 5,223,409 | 6/1993 | Ladner et al. | 435/69.1 |
| 5,270,170 | 12/1993 | Schatz et al. | 435/7.37 |
| 5,395,750 | 3/1995 | Dillon et al. | 435/5 |
| 5,403,484 | 4/1995 | Ladner et al. | 435/69.1 |
| 5,432,018 | 7/1995 | Dower | 435/5 |
| 5,498,538 | 3/1996 | Kay et al. | 435/69.1 |
| 5,571,698 | 11/1996 | Ladner et al. | 435/69.1 |

FOREIGN PATENT DOCUMENTS 2285446  7/1995  United Kingdom .

OTHER PUBLICATIONS

Wada et al., Biochemical and Biophysical Research Communications, vol. 213, No. 3, pp. 1091–1098, Aug. 1995.
Zhang et al. Functional evidence that transmembrane 12 and the loop domain between transmembrane 11 and 12 form part of the drug–binding domain in P–glycoprotein encoded by MDR1. The Journal of Biological Chemistry, vol. 270, No. 10, pp. 5441–5448, Mar. 10, 1995.
Smith et al. Libraries of peptides and proteins displayed on filmentous phage. Methods in Enzymology. vol. 217, pp. 228–257, 1993.
Adey et al. (1995). *Gene* 156 : 27–31.
Boer et al. (1995). *Proc. Amer. Ass. Cancer Res.* 36: 331.
Cwirla et al. (1990). *Proc. Natl. Acad. Sci. USA* 87: 6378–6382.

(List continued on next page.)

*Primary Examiner*—Keith MacMillan
*Assistant Examiner*—P. Ponnaluri
*Attorney, Agent, or Firm*—Mathews, Collins, Shepherd & Gould, P.C.

[57] ABSTRACT

The present invention describes peptides capable of specifically binding to preselected micromolecules or to their natural receptor. The preselected molecules include but are not limited to drugs, vitamins, neuromediators and steroid hormones. Methods of using the phage display libraries to identify peptide compositions in preselected binding interactions are also disclosed. The retrieved peptides mimicking a natural receptor binding site to preselected molecules are used as is or as ligands to re-screen the same or different libraries to find and/or derive new receptor ligands, or are used to elicit the production of antibodies capable of binding to the natural receptor. The two categories of effector molecules (peptides or antibodies) may find diagnostic, therapeutic or prophylactic uses. The peptides directly derived from the phage display libraries may be used as drug detectors or antidotes. The others may be used to identify, target, activate or neutralize the receptor for the preselected micromolecules, the receptor being known or unknown.

13 Claims, 9 Drawing Sheets

OTHER PUBLICATIONS

Devlin et al. (1990). *Science* 249: 404–406.
Dower et al. (1988). *Nucleic Acids Res.* 16: 6127–6145.
Felici et al. (1993). *Gene* 128: 21–27.
Felici et al. (1991). *J. Mol. Biol.* 222: 301–310.
Fodor et al. (1991). *Science* 251: 767–775.
Geysen et al. (1984). *Proc. Natl. Sci. USA* 81: 3998–4002.
Hanahan (1983). *J. Mol. Biol.* 166: 557–580.
Houghten et al. (1991). *Nature* 354: 84–86.
Lam et al. (1991). *Nature* 354: 82–84.
Luzzago et al. (1993). *Gene* 128: 51–57.
Maeji et al. (1992). *J. Immunol. Methods* 146: 83–90.
Motti et al. (1994). *Gene* 146: 191–198.
O'Neil et al. (1992). *Proteins: Structure, Function and Genetics* 14: 509–515.
Parmley & Smith (1988). *Gene* 73: 305–318.
Sato et al. (1984). *Infect. Immun.* 46: 422–428.
Scott and Smith (1990). *Science* 249: 386–390.
Smith (1985), *Science* 228: 1315–1317.
*Curr. Protocols Mol. Biol.* (1994).

| Isolates | Elution | Displayed Peptides | Frequency | HP Index | SEQ. ID. No. |
|---|---|---|---|---|---|
| V₁₂ | verapamil | TrpGlyArgPhe TrpGlyArgTrp LeuAla | 5 | 31 | 4 |
| V₆ | | ValCysAsp TrpTrpGlyTrp GlyIleCys | 3 | 29 | 3 |
| V₁₀ | | Tyr TrpMetGlyTrp LysTrpGluGlyGlu | 6 | 26 | 5 |
| V₁₅ | | TrpTrpAspPhe LeuGlnGlySerGluArg | 1 | 24 | 6 |
| V₂ | | PheAlaMetTrp TyrProLeuGlyTrpArg | 1 | 31 | 7 |
| A₆ | acid | ThrTrp TrpTrpThrTrp AlaGlyLysHis | 1 | 33 | 8 |
| A₄ | | Leu TrpSerProTrp GlyGlySerTrp | 9 | 30 | 9 |
| Motif | | Trp(Xaa)ₙ Trp, n = 1 or 2<br>Phe      Phe | | | 10 |
| High affinity consensus | | CysXaa TrpXaaXaaTrp XaaXaaCys | | | 11 |

FIG. 3

FIG. 7
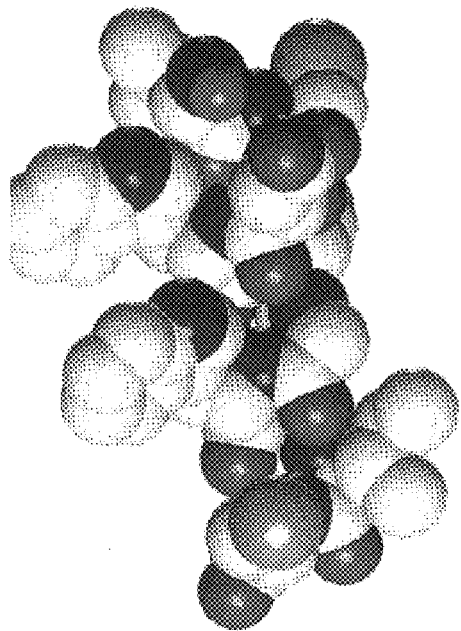
V6: VCDWWGWGIC
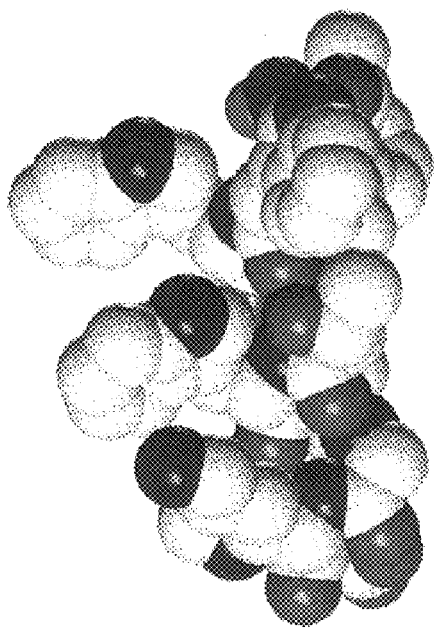
A4: LWSPWYGGSW
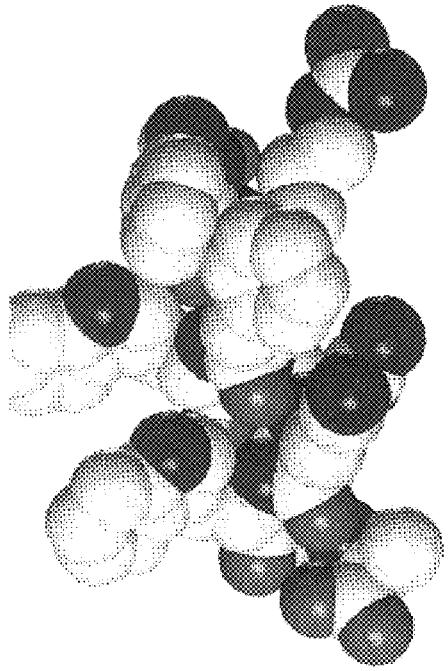
V12: WGRFWGRWLA
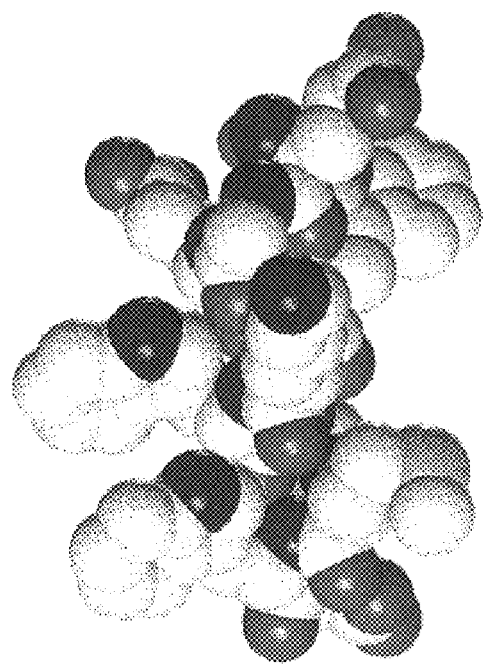
V10: YWMGWKWEGE

SEQUENCE LISTING

```
(1) GENERAL INFORMATION:

(iii) NUMBER OF SEQUENCES: 38

(2) INFORMATION FOR SEQ ID NO:1:

(i) SEQUENCE CHARACTERISTICS:
          (A) LENGTH: 99 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:1:

CGCTGGCCGA CGTGGCCNNK NNKNNKNNKN NKNNKNNKNN KNNKNNKGCG GCCTCTGAGG     60

CCTCTGAGGC CACGTAATAC ACGTGGCCTC AGAGGCCGC                            99

(2) INFORMATION FOR SEQ ID NO:2:

(i) SEQUENCE CHARACTERISTICS:
```

(A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:2:

TGAATTTTCT GTATGAGG                               18

(2) INFORMATION FOR SEQ ID NO:3:

(i) SEQUENCE CHARACTERISTICS:
            (A) LENGTH: 10 amino acids
            (B) TYPE: amino acid
            (C) STRANDEDNESS:
            (D) TOPOLOGY: circular (ii) MOLECULE TYPE: peptide (xi) SEQUENCE DESCRIPTION: SEQ ID NO:3:

Val Cys Asp Trp Trp Gly Trp Gly Ile Cys
1               5                   10

(2) INFORMATION FOR SEQ ID NO:4:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:4:

Trp Gly Arg Phe Trp Gly Arg Trp Leu Ala
1               5                   10

(2) INFORMATION FOR SEQ ID NO:5:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

Tyr Trp Met Gly Trp Lys Trp Glu Gly Glu
1               5                   10

(2) INFORMATION FOR SEQ ID NO:6:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Trp Trp Asp Phe Leu Gln Gly Ser Glu Arg
1               5                   10

(2) INFORMATION FOR SEQ ID NO:7:

(i) SEQUENCE CHARACTERISTICS:

(A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Phe Ala Met Trp Tyr Pro Leu Gly Trp Arg
1               5                   10

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Thr Trp Trp Trp Thr Trp Ala Gly Lys His
1               5                   10

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Leu Trp Ser Pro Trp Gly Gly Ser Trp
1               5

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "W/F"

(ix) FEATURE:
        (A) NAME/KEY: Modified-site
        (B) LOCATION: 4
        (D) OTHER INFORMATION: /product= "W/F"

(xi) SEQUENCE DESCRIPTION: SEQ ID NO:10:

Xaa Xaa Xaa Xaa
1

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO:11:

Cys Xaa Trp Xaa Xaa Trp Xaa Xaa Cys
1               5

(2) INFORMATION FOR SEQ ID NO:12:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:12:

GGGCCTGTNN BNNBNNBNNB NNBNNBNNBN NBNNBNNBTG CGGCGCTCTG            50

(2) INFORMATION FOR SEQ ID NO:13:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:13:

ACAGGCCCCG T                                                     11

(2) INFORMATION FOR SEQ ID NO:14:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

AAGGGCCGCA                                                       10

(2) INFORMATION FOR SEQ ID NO:15:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..20
            (D) OTHER INFORMATION: /product= "Xaa may comprise
                bewtween two and twenty"

(xi) SEQUENCE DESCRIPTION: SEQ ID NO:15:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

(2) INFORMATION FOR SEQ ID NO:16:

(i) SEQUENCE CHARACTERISTICS:
            (A) LENGTH: 22 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..22
            (D) OTHER INFORMATION: /product= "Xaa may comprise between
                two and twenty"

(xi) SEQUENCE DESCRIPTION: SEQ ID NO:16:

Cys Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Cys
             20

(2) INFORMATION FOR SEQ ID NO:17:

(i) SEQUENCE CHARACTERISTICS:
            (A) LENGTH: 44 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..44
            (D) OTHER INFORMATION: /product= "Xaa may comprise between
                two and twenty"

(xi) SEQUENCE DESCRIPTION: SEQ ID NO:17:

Cys Cys Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Cys Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Cys
         35                  40

(2) INFORMATION FOR SEQ ID NO:18:

(i) SEQUENCE CHARACTERISTICS:
            (A) LENGTH: 66 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..66
            (D) OTHER INFORMATION: /product= "Xaa may comprise between
                two and twenty"

(xi) SEQUENCE DESCRIPTION: SEQ ID NO:18:

Cys Cys Xaa Xaa Xaa Xaa Xaa Xaa Xaa Xaa Xaa Xaa Xaa Xaa Xaa Xaa
  1               5                  10                  15

Xaa Xaa Xaa Xaa Xaa Cys Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Cys Xaa Xaa Xaa Xaa Xaa
         35                  40                  45

```
Xaa Xaa Xaa Xaa Xaa Xaa Xaa Xaa Xaa Xaa Xaa Xaa Xaa Xaa Xaa
    50                  55                  60

Cys Cys
65
```

(2) INFORMATION FOR SEQ ID NO:19:

(i) SEQUENCE CHARACTERISTICS:
        (A) LENGTH: 87 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..87
        (D) OTHER INFORMATION: /product= "Xaa may comprise between
            two and twenty"

(xi) SEQUENCE DESCRIPTION: SEQ ID NO:19:

```
Cys Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Cys Xaa Xaa Xaa Xaa Xaa Xaa Xaa Xaa
            20                  25                  30

Xaa Xaa Xaa Xaa Xaa Xaa Xaa Xaa Xaa Xaa Cys Xaa Xaa Xaa Xaa
            35                  40                  45

Xaa Xaa Xaa Xaa Xaa Xaa Xaa Xaa Xaa Xaa Xaa Xaa Xaa Xaa Xaa
    50                  55                  60

Cys Xaa Xaa Xaa Xaa Xaa Xaa Xaa Xaa Xaa Xaa Xaa Xaa Xaa Xaa
65                  70                  75                  80

Xaa Xaa Xaa Xaa Xaa Cys Cys
            85
```

(2) INFORMATION FOR SEQ ID NO:20:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /product= "decapeptide bank"

(xi) SEQUENCE DESCRIPTION: SEQ ID NO:20:

```
Xaa Xaa Xaa Xaa Xaa Xaa Xaa Xaa Xaa Xaa
1               5                   10
```

(2) INFORMATION FOR SEQ ID NO:21:

(i) SEQUENCE CHARACTERISTICS:
        (A) LENGTH: 9 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO:21:

```
Cys Xaa Xaa Xaa Xaa Xaa Xaa Xaa Cys
1               5
```

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Trp Xaa Xaa Trp
1

(2) INFORMATION FOR SEQ ID NO:23:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..60
        (D) OTHER INFORMATION: /product= "NNK codon may comprise
             from two to at least about twenty"

(xi) SEQUENCE DESCRIPTION: SEQ ID NO:23:

NNKNNKNNKN NKNNKNNKNN KNNKNNKNNK NNKNNKNNKN NKNNKNNKNN KNNKNNKNNK      60

(2) INFORMATION FOR SEQ ID NO:24:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..60
        (D) OTHER INFORMATION: /product= "NNB codon may comprise
             from two to at least about twenty"

(xi) SEQUENCE DESCRIPTION: SEQ ID NO:24:

NNBNNBNNBN NBNNBNNBNN BNNBNNBNNB NNBNNBNNBN NBNNBNNBNN BNNBNNBNNB      60

(2) INFORMATION FOR SEQ ID NO:25:

(i) SEQUENCE CHARACTERISTICS:
        (A) LENGTH: 3 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

Trp Xaa Trp
1

(2) INFORMATION FOR SEQ ID NO:26:

(i) SEQUENCE CHARACTERISTICS:

```
            (A) LENGTH: 12 amino acids
            (B) TYPE: amino acid
            (C) STRANDEDNESS:
            (D) TOPOLOGY: circular (ii) MOLECULE TYPE: peptide (xi) SEQUENCE DESCRIPTION: SEQ ID NO:26:

Cys Xaa Xaa Xaa Xaa Xaa Xaa Xaa Xaa Xaa Xaa Cys
1               5                   10

(2) INFORMATION FOR SEQ ID NO:27:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:27:

Cys Xaa Xaa Xaa Xaa Xaa Xaa Cys
1               5

(2) INFORMATION FOR SEQ ID NO:28:

(i) SEQUENCE CHARACTERISTICS:
            (A) LENGTH: 86 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..86
            (D) OTHER INFORMATION: /product= "Xaa may comprise between
                  two and twenty"

(xi) SEQUENCE DESCRIPTION: SEQ ID NO:28:

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Cys Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Cys Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Cys Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Cys
            85

(2) INFORMATION FOR SEQ ID NO:29:

(i) SEQUENCE CHARACTERISTICS:
            (A) LENGTH: 29 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:29:

TCGGCCGACG TGGCCTGGCC TCTGGGGCC                                   29
```

(2) INFORMATION FOR SEQ ID NO:30:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

```
CGCTGGCCGA CGTGGCCNNK NNKNNKNNKN NKNNKNNKNN KNNKNNKGCG GCCTCTGAGG    60

CCTCTGAGGC CACGTAATAC ACGTGGCCTC AGAGGCCGCM NNMNNMNNMN NMNNMNNMNN   120

MNNMNNMNNG GCCACGTCGG CCAGCG                                       146
```

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:31:

```
GGGCCTCGGC CGACG                                                    15
```

(2) INFORMATION FOR SEQ ID NO:32:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:32:

```
CGGCCGAGGC CCCAG                                                    15
```

(2) INFORMATION FOR SEQ ID NO:33:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:33:

```
TCGGCCGACG TGGCCNNKNN KNNKNNKNNK NNKNNKNNKN NKNNKGCGGC CTCTGGGGCC    60
```

(2) INFORMATION FOR SEQ ID NO:34:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

```
GGGCCTGTNN BNNBNNBNNB NNBNNBNNBN NBNNBNNBTG CGGCGCTTCT G             51
```

(2) INFORMATION FOR SEQ ID NO:35:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:35:

ACAGGCCCCG T                                                           11

(2) INFORMATION FOR SEQ ID NO:36:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:36:

AAGCGCCGCA                                                             10

(2) INFORMATION FOR SEQ ID NO:37:

(i) SEQUENCE CHARACTERISTICS:
      (A) LENGTH: 66 base pairs
      (B) TYPE: nucleic acid
      (C) STRANDEDNESS: double
      (D) TOPOLOGY: linear (ii) MOLECULE TYPE: DNA (xi) SEQUENCE DESCRIPTION: SEQ ID NO:37:

TCGGCCGACG GGGCCTGTNN BNNBNNBNNB NNBNNBNNBN NBNNBNNBTG CGGCGCTTCT      60

GGGGCC                                                                 66

(2) INFORMATION FOR SEQ ID NO:38:

(i) SEQUENCE CHARACTERISTICS:
      (A) LENGTH: 12 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:38:

Xaa Xaa Xaa Xaa Xaa Xaa Xaa Xaa Xaa Xaa Cys Cys
1               5                   10

METHODS OF GENERATING NOVEL PEPTIDES

The present invention relates to methods of generating novel peptides capable of specific binding to preselected micromolecules or to their natural receptors.

FIELD OF THE INVENTION

The present invention relates generally to methods for selecting peptide ligands to molecules of interest and, more particularly, to methods for generating and screening large phage display libraries for peptides with desired binding characteristics to micromolecules including but not limited to drugs, vitamins, neuromediators, and steroid hormones. Peptides encoded by the libraries are expressed as fusion proteins of bacteriophage coat proteins, and bacteriophages are then screened against the molecules of interest. Peptides mimicking the natural or artificial receptor site for micromolecules of choice may then be used in turn to reiterate the screening of the same or different library to find a peptide ligand or effector molecule. Peptide ligands having a wide variety of uses, such as therapeutic, diagnostic or prophylactic reagents, will thus be identified without any prior information on the structure of the expected receptor. Alternatively, the peptides mimicking the receptor site can be used as antigens to elicit the production of antibodies, another type of effector molecule.

BACKGROUND OF THE INVENTION

There is an increasing need to find new molecules which can effectively modulate a wide range of biological processes, for applications in medicine and agriculture. A standard way for searching for novel bioactive chemicals is to screen collections of natural materials, such as fermentation broths of plant extracts, or libraries of synthesized molecules using assays which can range in complexity from simple binding reactions to elaborate physiological preparations. The screens often only provide leads which then require further improvement either by empirical methods or by chemical design. The process is time-consuming and costly, but it is unlikely to be totally replaced by rational methods even when they are based on detailed knowledge of the chemical structure of the target molecules. Thus, what we might call "irrational drug design"—the process of selecting the right molecules from large ensembles or repertoires—requires continual improvement both in the generation of repertoires and in the methods of their selection.

Recently, there have been several developments in using peptides or nucleotides to provide libraries of compounds for lead discovery. The methods were originally developed to speed up the determination of epitopes recognized by monoclonal antibodies. For example, the standard serial process of stepwise search of synthetic peptides now encompasses a variety of complex methods in which large arrays of peptides are synthesized in parallel and screened with acceptor molecules labelled with fluorescent or other reporter groups. The sequence of an effective peptide can be decoded from its address in the array. See for example Geysen et al., *Proc. Natl. Acad. Sci. USA,* 81: 3998–4002 (1984); Maeji et al., *J. Immunol. Methods,* 146: 83–90 (1992); and Fodor et al., *Science,* 251: 767–775 (1991).

In another approach, Lam et al., *Nature,* 354: 82–84 (1991) describe combinatorial libraries of peptides that are synthesized on resin beads such that each resin bead contains about 20 pmoles of the same peptide. The beads are screened with labelled acceptor molecules and those with bound acceptor are searched for by visual inspection, physically removed, and the peptide identified by direct sequence analysis. This method requires, however, sensitive methods for sequence determination.

A different approach for identification in a combinatorial peptide library is used by Houghten et al., *Nature,* 354: 84–86 (1991). For hexapeptides of the twenty natural amino acids, four hundred separate libraries are synthesized, each with the first two amino acids fixed and the remaining four positions occupied by all possible combinations. An assay, based on competition for binding or other activity, is then used to find the library with an active peptide. Then twenty new libraries are synthesized and assayed to determine the effective amino acid in the third position, and the process is repeated until all six positions in the peptide are identified.

More recently, Houghten (Abstract, European Peptide Society 1992 symposium, Interlaken, Switzerland) suggested a different approach. Starting with twenty amino acids, a total of 20×6=120 peptide mixtures are synthesized. In twenty mixtures, position 6 contains a unique amino acid, and positions 1–5 contain a mixture of all natural amino acids. In another twenty mixtures, position 5 contains a unique amino acid and all other positions contain a mixture of all twenty amino acids, etc. Once synthesized, all the 120 peptide mixtures are tested simultaneously and the most active of each of the twenty mixtures representing each position is identified.

A biological method has recently been described in which a library of peptides is presented on the surface of a bacteriophage such that each phage contains a DNA sequence that codes for an individual peptide. The library is made by synthesizing a large number of random oligonucleotides to generate all combinations, followed by their insertion into a phage vector. Each of the sequences is cloned in one phage and the relevant peptide can be selected by finding those that bind to the particular target (by a method known as biopanning). The phages recovered in this way can be amplified and the selection repeated. The sequence of the peptide is decoded by DNA sequencing. See for example Cwirla et al., *Proc. Natl. Acad. Sci. USA,* 87: 6378–6382 (1990); Scott et al., *Science,* 249: 386–390 (1990); and Devlin et al., *Science,* 249: 404–406 (1990).

These libraries may encompass a very large number of different peptides which represent potential ligands to a variety of macromolecules such as receptors, polypeptides, enzymes, carbohydrates and antibodies. Therefore, phage display technology appears to be a very powerful tool for the selection of peptide sequences that bind to a target molecule. These peptides may find numerous applications, namely as antigens in vaccine composition, as enzyme inhibitors, as antagonists or agonists to receptors, for example.

For example, the monoclonal antibody 1B7, first described by Sato et al. (*Infect. Immun.,* 46: 422–428 (1984)) has been raised against the *Bordetella pertussis* toxin (PTX). This antibody is able to neutralize the toxin in vitro and to protect mice from intracerebral challenge with virulent *B. pertussis*. The epitope recognized by 1B7 was shown to be discontinuous and largely dependent on conformation. Hoping to obtain peptide sequences that would mimic such a discontinuous epitope, Felici et al. (*Gene,* 128: 21–27(1993)) constructed two phage display libraries consisting of nine random amino acids inserted in the major coat protein (pVIII), which nanopeptides were linear or flanked by two cysteine residues (circular). The two libraries were screened with the antibody 1B7. The positive clones were sequenced and a consensus sequence was obtained only for linear peptides. In the absence of a three-dimensional structure of the PTX, it is very difficult to determine how the consensus peptide sequence corresponds to amino acid residues of the original protein that are important in the constitution of the discontinuous epitope recognized by the antibody 1B7. Despite this lack of information, the authors expected that the selected nanopeptides would mimic the binding site of the original protein sufficiently to serve as antigens in the production of vaccines against PTX. This was not the case. Indeed, the peptides were able to compete with PTX for the binding site of 1B7, but they were not capable of sufficiently mimicking the discontinuous epitope of PTX to elicit the production of antibodies specific to the original antigen, PTX. Moreover, it is believed that the phage recombinant peptides adopt a conformation that may be governed by the surrounding phage sequences, which conformation is recognizable by 1B7. When peptides alone were synthesized without the presence of surrounding phage sequences, they lost their ability to bind 1B7. It is suggested that more sophisticated or longer peptides might be constructed and might be more successful in mimicking the original epitope.

The same group of researchers (Luzzago et al., *Gene*, 128:51–57 (1993)) used the same libraries to select oligopeptides that would bind another antibody, H107, that recognizes the native conformation of the recombinant human H-subunit ferritin (H-Fer). This time, the three-dimensional structure of H-Fer was known. The consensus peptide sequence obtained only for the linear selected peptides was used to assign to amino acids, that were space located in the original protein, a putative role in the conformation of the H-Fer epitope. When the peptides were synthesized in the presence of surrounding sequences located in the original protein as well as those synthesized with surrounding phage sequences, the peptides screened with H107 antibody were capable of mimicking the original proteic assembly and bound H107. Accordingly, the different results obtained with peptides selected with two different antibodies suggest that the same libraries were not successful in the selection of epitopes of all existing antigens.

A different shorter peptide library has been obtained by O'Neil et al. (*Proteins: Structure, Function and Genetics*, 14: 509–515 (1992)). These authors have constructed a random circular hexapeptide sequence inserted in the pIII phage protein. This time, the library was used to select ligands to the receptor glycoprotein IIb/IIIa, a member of the integrin family of cell adhesion molecules that mediate platelet aggregation through the binding of fibrinogen and von Willebrand factor. The purpose of this work was to find ligands useful as antagonists or as antithrombotic agents. The glycoprotein IIb/IIIa binds to a very short sequence commonly known as the RGD sequence. These authors identified a consensus sequence when using a circular library, and identified certain ligands that were better antagonists than the ligand SK106760 (a cyclic peptide developed after extensive array of peptides) used to elute the phages of interest. They also found that a variant RGD sequence wherein the arginine was replaced by a lysine was a strong anti-aggregatory peptide.

Another "genetic" method has been described where the libraries are the synthetic oligonucleotides themselves wherein active oligonucleotide molecules are selected by binding to an acceptor site and are then amplified by the polymerase chain reaction (PCR). PCR allows serial enrichment, and the structure of the active molecules is then decoded by DNA sequencing of clones generated from the PCR products. The repertoire is limited to nucleotides and the natural pyrimidine and purine bases or those modifications that preserve specific Watson-Crick pairing and can be copied by polymerase.

The main advantage of the genetic methods resides in the capacity for cloning and amplification of DNA sequences, which allows enrichment by serial selection and provides a simple and easy method for decoding the structure of active molecules. The prior art results show little success in selecting peptides for a specific molecule, since the length and the conformation of the exposed peptide may be sufficient to retrieve a peptide binding to a specific molecule while it might not be suited to retrieve a peptide that efficiently mimics a more sophisticated binding region on another molecule.

There is therefore a need for other libraries that contain novel peptide sequences at the surface of filamentous phages, which libraries may be used to select ligands to known and unknown molecules. There is also a need for more rational approach to construct libraries suitable for retrieving the best diversity of peptides binding to any ligand.

Furthermore, to date there has been no use of this technology to find peptides that are capable of binding to micromolecules and of mimicking a natural receptor site, and to use these peptides as is or as a second ligand to re-screen libraries to find a new image of the receptor, or as an immunogen to produce antibodies which are another class of effector molecules.

STATEMENT OF THE INVENTION

It is an object of the present invention to provide phage display libraries consisting of random linear or circular peptides forming one or more loops that are expressed in the protein pIII, or other proteins, of a filamentous phage. In one embodiment of this invention, we provide a linear decapeptide phage display library. The linear library has been successfully used to select diverse peptides.

A bacterial host comprising this vector is also provided.

It is an another object of the invention to provide a method for producing a peptide effector molecule capable of binding a micromolecule comprising:

a) obtaining a random bacteriophage library wherein said bacteriophage express fusion proteins comprising at least one random peptide sequence joined to a bacteriophage exposed protein;

b) screening said library with a first ligand comprising a preselected micromolecule;

c) retrieving at least one bacteriophage expression a first peptide family member mimicking a natural acceptor binding site to said preselected micromolecule; and d) obtaining the amino acid sequence of at least one of said peptides of said first peptide family, and synthesizing said peptide or a derivative thereof.

In the above method, the preselected micromolecule is selected from, but not limited to, drugs, vitamins, neuromediators, steroid hormones, an oligopeptide mimicking a natural acceptor binding site to preselected molecules.

"Acceptor binding site" as defined herein refers to a site of conformation such that it matches the conformation of a preselected target molecule. Therefore, such an acceptor site is a short peptide sequence representing the portion (continuous or discontinuous) of a macromolecule binding site to a target molecule. The macromolecules are usually, but are not limited to, antibodies or receptors.

In screening a library, a preselected micromolecule may be a drug, for example doxorubicin. The retrieved peptides then mimic the natural receptor site to this drug, for example a MDR-receptor. These peptides or derivatives thereof are then synthesized and used as is. The synthesized peptides can alternatively be used in turn as preselected micromolecules to screen the same or another library to retrieve another set of peptides, in which case the acceptor binding site is a new image of the preselected molecule used in the first instance, for example a doxorubicin peptide analog. The synthesized peptides are also alternatively used as immunogens to elicit the production of antibodies used to detect, target, activate or neutralize the natural acceptor molecule.

Such antibodies are useful as diagnostic, therapeutic or prophylactic reagents and are also useful as binding reagents, on affinity columns or on antibody-coated plates for example, to identify or target and/or to purify a natural receptor. When used as a diagnostic, therapeutic or prophylactic reagents, the antibodies may be used as whole entities, as $(Fab)_2$ or as $F(ab')$ fragments. The antibodies may be directly labelled, coupled to a first reactive member, which first member reacts with a second labelled reactive member, or may be reacted with a labelled anti-species antibody (indirect immunoassay). The use of any label known in the art is contemplated.

The arrangement of random peptide sequence takes different forms comprising:

$(X)_n$ (SEQ ID NO:15)

C—$(X)_n$—C (SEQ ID NO:16)

CC—$(X)_{n1}$—C—$(X)_{n2}$—C (SEQ ID NO:17)

CC—$(X)_{n1}$—C—$(X)_{n2}$—C—$(X)_{n3}$—CC (SEQ ID NO:18); or

CC—$(X)_{n1}$—C—$(X)_{n2}$—C—$(X)_{n3}$—C$(X)_{n4}$—CC (SEQ ID NO:19)

wherein C is cysteine, X is any one of the twenty naturally encountered amino acids, each of n, $n_1$, $n_2$, $n_3$ and $n_4$ is an integer comprising between two and twenty and each occurrence of X is the same or different.

When using doxorubicin in the above-method, a diversity of peptides have been obtained after screening a linear decapeptide bank $(X)_{10}$ (SEQ ID NO:20). They share the following consensus motif:

W/F—$(X)_n$—W/F, wherein W/F is either tryptophan or phenylalanine, X is any one of the twenty naturally encountered amino acids, each occurrence of X being the same or different, and n is 1 or 2.

The binding to doxorubicin was displaced by two different MDR-inducing drugs verapamil and vinblastine. This displacement indicates that the clones which bind to doxorubicin encode peptides that represent the binding site of a receptor involved in multiple drug resistance (MDR).

Oligopeptides (less than or equal to 50 amino acids) comprising this motif are provided as an other object of the invention, as well as their coding nucleic acids.

The peptides having the highest specific binding affinity have the following structure or formula:

C—X—W—X—X—W—X—X—C (SEQ ID NO:11), wherein C is cysteine, W is tryptophan, and X is any one of the twenty naturally encountered amino acids, each occurrence of X being the same or different.

Oligopeptides (less than or equal to 50 amino acids) comprising this structure are provided as an other object of the invention, as well as their coding nucleic acids.

It is worthwhile noting that a circular peptide which consensus sequence is C—$(X)_7$—C (SEQ ID NO:21) is deducible for the above oligopeptide which has been shown to be the best ligand to doxorubicin, provided that it contains the motif W—X—X—W (SEQ ID NO:22). Since a circular decapeptide library has been unsuccessfully screened against doxorubicin, this indicates that constrained peptide sequences are more capricious in their ability to bind a preselected molecule. In view of these results, heptapeptide circular libraries are considered as a specific embodiment of this invention to retrieve at least a doxorubicin binding peptide.

The above methods provide peptide ligands to the MDR-receptor and are further applicable to the identification of a diversity of effector molecules to an also diversified receptor population or to other acceptor molecules in general.

DETAILED DESCRIPTION OF THE INVENTION

The present invention provides novel methods and compositions for identifying peptides which bind to preselected drugs or to their natural receptor. FIG. 9 is a schematic representation of the present invention. When a phage display library is screened with a micromolecule binding to a known receptor (opoids and steroids, for example), the binding phage display peptides are then sequenced, synthesized and used as a drug binding tool to detect drugs in biological samples such as blood and urine, or as a drug antidote. The synthesized peptides may be alternatively used to re-screen the same or another library to retrieve novel effector molecules which are analogs of the micromolecules of interest used in first instance. The new effector molecules will possess therapeutic or prophylactic use by activating or neutralizing the natural receptor, or a diagnostic use by targeting and detecting the same receptor. Alternatively, the synthesized peptides may be used to elicit the production of antibodies useful as other effector molecules having therapeutic, prophylactic or diagnostic uses. When the preselected molecule binds to an unknown receptor, the same principles apply. Additionally, the peptides on phages may be used directly as immunogens to elicit the production of antibodies.

In one embodiment, the invention relates to methods for identifying the peptides capable of binding to a preselected micromolecule. In certain aspects, the methods generally comprise construction of an oligonucleotide library of at least about $10^8$ members which encode the peptides. Each library member is joined in a reading frame to the 5' region of a nucleotide sequence encoding an outer structural protein of the bacteriophage (minor coat proteins). Appropriate host cells are transformed with the expression vectors, generally by electroporation, and the transformed cells cultured under conditions suitable for expression and assembly of bacteriophages. Using an affinity screening process (i.e., biopanning), bacteriophage library members are exposed to the preselected micromolecule under conditions conductive to a specific binding, and bacteriophages whose minor coat proteins have peptides which bind the micromolecule are selected. The nucleotide sequence which encodes the peptide on the selected phage may then be determined by sequencing. By repeating the affinity selection process one or more times, the peptides of interest may be enriched. By increasing the stringency of the selection, e.g., by reducing the valency of the interaction towards substantial monovalency, peptides of increasingly higher affinity can be identified.

In another aspect, the methods are concerned with expression vectors having the oligonucleotide library members joined in a reading frame with a nucleotide sequence to encode a fusion protein, wherein the library member represents the 5' member of the fusion and the 3' member comprises at least a portion of an outer structural protein of the bacteriophage. The first residue of the peptide encoded by the library member may be at the 5'-terminus of the sequence encoding the phage coat protein. In preferred embodiments, where phage proteins are initially expressed as pre-proteins and then processed by the host cell to a mature protein, the library members are inserted so as to leave the peptide encoded thereby at the N-terminus of the phage coat protein after processing or a protein substantially homologous thereto.

The invention also concerns host cells transformed with a bacteriophage expression vector having an oligonucleotide library member, joined in the reading frame to the 5' region of the nucleotide sequence encoding an outer structural protein of the bacteriophage, wherein the library member encodes a peptide of at least two to about eighty-six amino acids (four units of twenty amino acids plus terminating and intercalated cysteine residues).

Generally, the oligonucleotide libraries of the invention comprise a variable codon region which codes for the peptides of interest, and optimally comprise sequences coding for one or more spacer amino acids residues such as Gly or Ala. The variable region may be encoded by $(NNK)_n$ (SEQ ID NO:23) or $(NNB)_n$ (SEQ ID NO:24) where N is A, C, G, or T; K is G or T; B is G, T or C, and n is from two to at least about 20. In a preferred embodiment, the variable region of the oligonucleotide library member encodes a decapeptide. The variable codon region may also be prepared from a condensation of activated trinucleotides.

In accordance with the present invention, novel libraries have been developed to reveal new effectors to target molecules. More particularly, we have obtained peptides that may represent discontinuous amino acids constituting MDR-binding sites using a decapeptide linear library.

Moreover, while other groups have sought ligands to macromolecules such as receptors, we have, on the contrary, used these libraries to seek ligands to micromolecules. For example, peptides have been obtained which bind different MDR-inducing molecules, including doxorubicin, verapamil and vinblastine.

The present invention will be described hereinbelow by way of the following Examples and appended Figures, which purpose is to illustrate the invention rather than to limit its scope.

BRIEF DESCRIPTION OF DRAWINGS

The file of this patent contains at least one drawing executed in color. Copies of this patent with color drawings will be provided by the Patent and Trademark Office upon request and payment of the necessary fee.

FIG. 3 shows the amino acid sequences (SEQ. ID. NOS.: 3 to 11, deduced from the DNA sequences) of the N-terminal peptides of pIII of twenty-six phages isolated by four rounds of biopanning on doxorubicin-BSA coated microtiter wells.

FIG. 7 (SEQ ID NOs:3, 4, 5, and 9) depicts the three-dimensional structure of four peptides, $A_4$ (SEQ ID NO:9), $V_6$ (SEQ ID NO:3), $V_{10}$ (SEQ ID NO:5) and $V_{12}$ (SEQ ID NO:4), exposed on their phages (hydrogen atoms are omitted).

REAGENTS & STRAINS

SfiI and BglI restriction endonucleases, T4 DNA ligase, T4 kinase, Klenow polymerase were obtained from Boehringer Mannheim. Sequenase T7 was obtained from Pharmacia. Doxorubicin was obtained from Sigma. Oligonucleotides were synthesized with an applied Biosystems PCR-Mate and purified on ODC columns (ABI). fUSE5 vector and E. coli MC1061, K802, K91Kan were provided by G. Smith, Univ. of Missouri, Columbia, Mo. and described in Smith et al., *Science*, 228: 1315–1317 (1985) and Parmley & Smith, *Gene*, 73: 305–318 (1988).

EXAMPLE 1

Construction of a Linear Oligonucleotide Library

Figure 1:
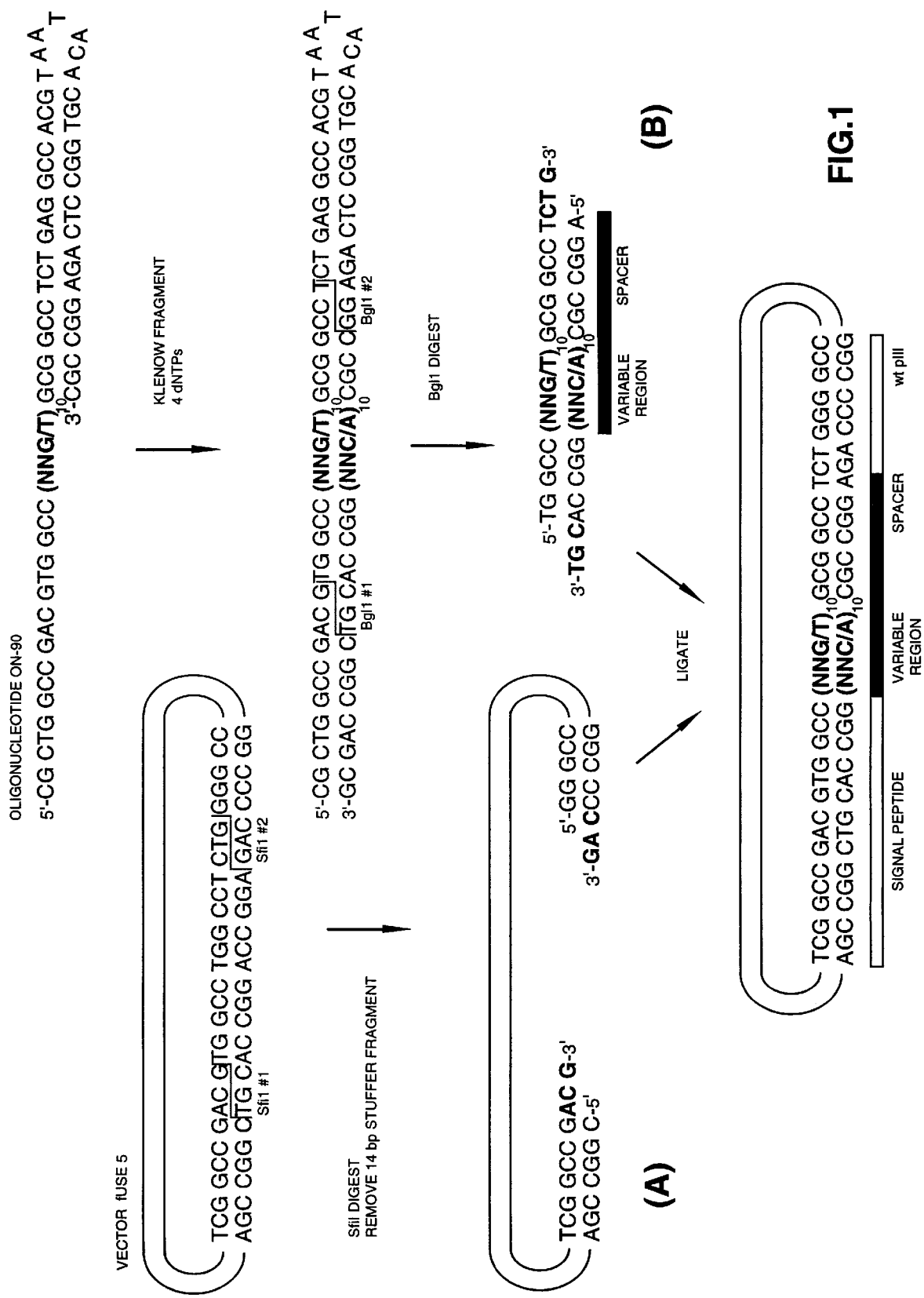
FIG. 1 (SEQ ID NOs:1 and 29–33) depicts the construction of a linear oligonucleotide library. (A) The vector, fUSE (SEQ ID NO:29), contains two non-complementary SfiI sites separated by a 14 bp "stuffer fragment". Removal of the SfiI fragment allows oriented ligation of oligonucleotides with the appropriate cohesive ends. (B) The oligonucleotide ON-90 (SEQ ID NO:1) was synthesized with a self-complementary 3' terminus and was elongated by extension of the 3' end with Klenow fragment. The cleavage of fill-in product with BglI released a fragment with cohesive termini complementary to SfiI sites in the vector. The BglI-cleaved fragment was ligated to the vector and electro-transformed into E.coli.

Oligonucleotides were synthesized, then inserted in the vector fUSE5. These oligonucleotides have the general structure shown in FIG. 1B. The 5' and 3' ends have a fixed sequence, chosen to reconstruct the amino acid sequence in the vicinity of the signal peptidase site. The central portion contained the variable regions which comprise the oligonucleotide library members, and may also code for spacer resides on either or both sides of the variable sequence. A collection of oligonucleotides encoding all possible decapeptides was synthesized with a self-complementary 3'-terminus [5'-CGCTGGCCGACGTGGCC(NNK)$_{10}$GCGGCCTCTGAGGCCTC TGAGGCCACGTAATA- CACGTGGCCTCAGAGGCC GC-3', SEQ. ID. NO.: 1, where N is A, C, G and T (nominally equimolar), and K is G and T (nominally equimolar)], while the complementary strand was synthesized by extension of the 3' end with Klenow polymerase. The SfiI compatible ends were generated by restriction enzyme digestion of 5 µg of fill-in product with 400 units of BglI in 50 µl, as recommended by the supplier. The desired fragment was electrophoresed on 15% (w/v) poly-acrylamide gel, and DNA of the correct size was then excised, recovered, and purified as described in Curr. Protocols Mol. Biol. (1994). The vector fUSE (100 µg) was digested to completion with SfiI and ethanol precipitated twice in the presence of 2 M ammonium acetate. This DNA could not be self-ligated, indicating complete removal of the 14-bp "stuffer" that lies between the SfiI sites. A total of 20 µg of SfiI digest of fUSE5 vector was then ligated with 200 ng of purified oligonucleotide insert (molar ratio 1:2) by an overnight incubation at 15 C. in 1 ml of T4 ligase buffer (20 mM Tris-HCl, pH 7.5, 5 mM $MgCl_2$, 2 mM DTT, 1 mM ATP) and 4000 units of T4 DNA ligase. The ligated DNA was ethanol precipitated in the presence of 0.3 M sodium acetate, resuspended in 40 pl of water, and transformed by electroporation into E. coli MC1061. Ten electro-transformations, each containing 80 µl of cell suspensions (final concentration $5 \times 10^{10}$ cells/ml) and 2 µg of DNA (500 µg/ml), were performed by pulsing at 12.5 kv/cm for 5 msec as described in Dower et al., Nucleic Acids Res., 16: 6127–6145 (1988). After electroporation, E. coli cells were allowed to non-selective outgrowth at 37 C for one hour in 2 ml of SOC medium [consisting of 2% Bacto tryptone, 0.5% Bacto yeast extract, 10 mM NaCl, 2.5 mM KC, 10 mM $MgCl_2$, 10 mM $MgSO_4$, 20 mM glucose; Hanahan, J. Mol. Biol., 166: 557–580 (1983) containing 0.2 mg/ml tetracycline. Aliquots (20 µl) of cells from each of the transformants were then removed and various dilutions plated on LB plates (Luria-Bertani medium) containing 40 mg/ml tetracycline to assess the transformation efficiency. The remainder of the cell suspension was used to inoculate one liter of L-broth containing tetracycline (20 mg/ml) and was grown through approximately 10 doublings at 37 C. to amplify the library.

Phages from liquid cultures were obtained by clearing the supernatant twice by centrifugation (8000 RPM for 10 min at 4 C.), and precipitation of phage particles with polyethylene glycol (final concentration 3.3% polyethylene glycol-8000, 0.4 M NaCl), and centrifugation as described above. Phage pellets were resuspended in TBS (50 mM Tris-HCl, pH 7.5, 150 mM NaCl) and stored at 4 C. A portion of the library was used to infect K91Kan cells that were plated at low density on LB tetracycline plates (40 mg/ml). To analyze the diversity of the peptide sequences in the library, twelve individual clones producing infectious phages were picked, and the DNA of their variable region was sequenced using sequenase T7 kit and an oligonucleotide sequencing primer fUSE$^{32}$P (5'-TGAATTTTCTGTATGAGG-3'), SEQ. ID. NO.: 2, which is complementary to the sequence located 32 nucleotides to the 3' side of the second Sfil site in the fUSE5 vector.

Figure 2:
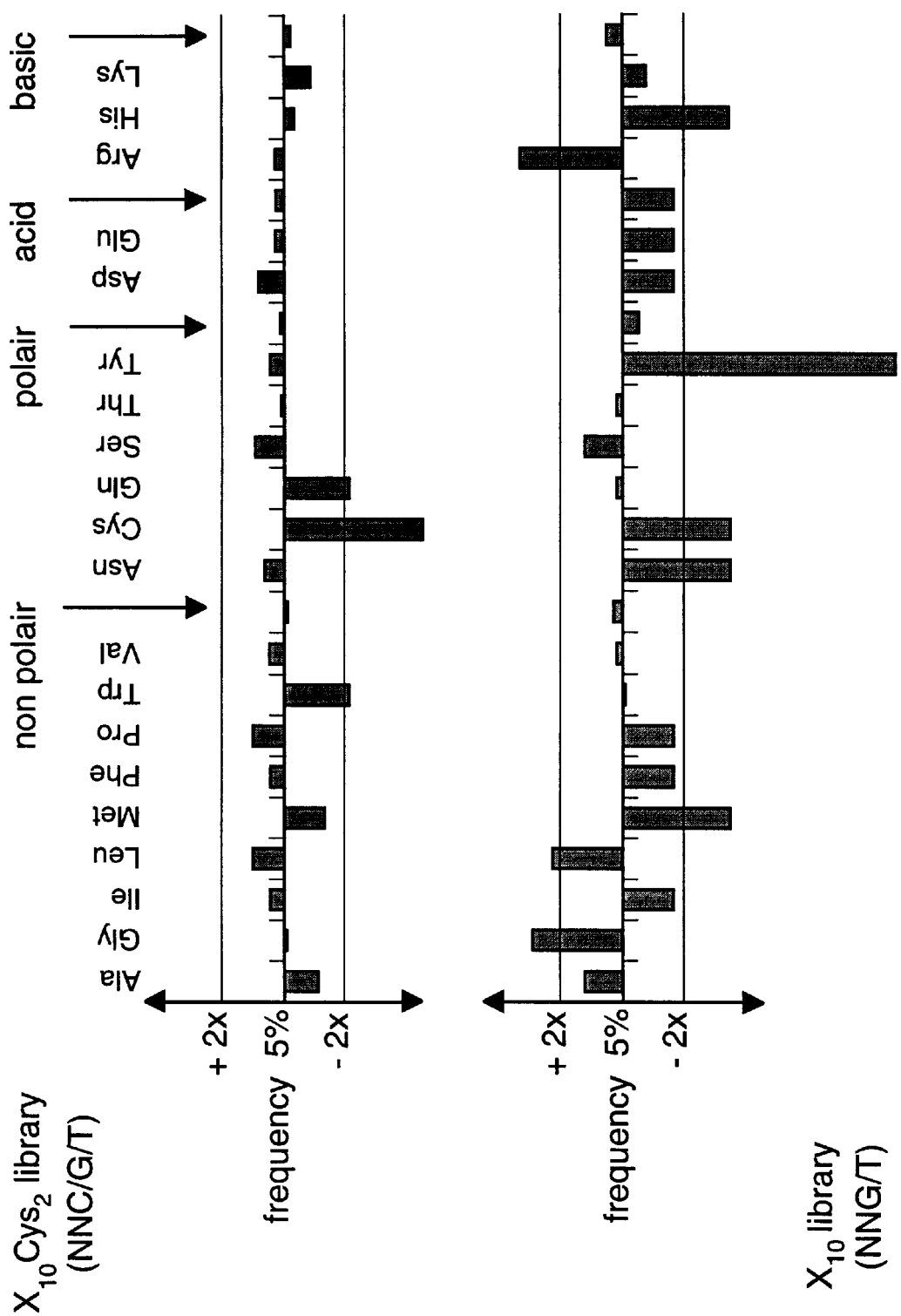
FIG. 2 (SEQ ID NOs:20 and 38) depicts the amino acid frequencies of the variable region observed in randomly chosen isolates for the linear and for the circular libraries. Individual isolates were sequenced with the oligo primer fUSE$^{32}$P, which is 32 nt downstream of the gene III cloning site of fUSE. 2X represents 100% deviation from the optimal frequency that is equal to 5%.

In FIG. 2, the amino acid frequencies are deduced for the peptides encoded by oligonucleotides inserts of a sample of randomly chosen, infectious phage.

Constructing a library of peptides displayed on the N-terminus of processed pIII necessarily alters the amino acids in the vicinity of the signal peptidase cleavage site. Certain changes in the corresponding region of the major coat protein, pVIII, have been shown to reduce processing efficiency, slowing or preventing the incorporation of pVIII to virions (Felici et al., J. Mol. Biol., 222: 301–310 (1991)). If pIII were similarly affected, the diversity of peptides contained in the library would be reduced (Parmley and Smith, Gene, 73: 305–313 (1988)). The finding that most amino acids appear at each position of the variable peptides of randomly chosen phage indicates that processing defects do not impose important constraints on the diversity of the library. Furthermore, it is indicative that the inserted sequence in the fusion protein does not deleteriously alter the biological properties of the bacteriophage protein.

EXAMPLE II

Biopanning

Doxorubicin was coupled to BSA (Manson, Methods in Mol. Biol., 10: 29–31 (1993)) by using glutaraldehyde as previously described. The doxorubicin-BSA conjugate was then diluted to 100 µg/ml in PBS, 50 µl of solution was then added to each well and used to select clones from a decapeptide library by successive rounds of biopanning on 96-well plates (Nunc maxisorb microtiter plate). Doxorubicin-BSA conjugate was then bound to the plate overnight at 4 C., the wells washed with PBS and blocked with 1% BSA in PBS for 1 h at room temperature. After blocking, the wells were washed six times with PBS, the $10^{10}$ phage particles per well of the primary decapeptide library were then added in 50 µl of 0.1% BSA/PBS and the plates were incubated for 1 h at room temperature. The plates were washed 12 times with PBS to remove non-specific phages (phages which express peptides without the desired specificity) and the bound phages were eluted by treatment with 50 µl of 0.1 M HCl (pH 2.2 adjusted with glycine) or with 50 µl of 50 mM of verapamil (competitor to doxorubicin). Neutralization of the eluate, titration, and amplifications on agar medium were carried out essentially as described in S. F. Parmley and G. P. Smith, Gene, 73: 305–313 (1988)). The binding and elution reactions were repeated several times. Recoveries of phages from this process are shown in FIG. 3, where the repeated selection of phages resulted in an enrichment of phages capable of binding to doxorubicin. These results indicated that phages of higher affinity were preferentially enriched in each panning step.

After four rounds of biopanning (five rounds in the case of acidic elution) and phage amplification, the individual phages derived from each elution screen were grown and their peptide-encoding regions sequenced. The amino acid sequences of these twenty-six phages that bound to doxorubicin is summarized in FIG. 3 (SEQ. ID. NOS.: 3 to 11). The most remarkable feature of the peptides selected by doxorubicin was that all twenty-six sequences contained Tryptophan (W), demonstrating a striking consensus sequence WXXW (SEQ ID NO:22) or WXW (SEQ ID NO:25), of which only two isolates did not contain a W residue from the left or the right side of the sequence, but in these clones, the tryptophan residue was replaced by another aromatic amino acid phenylalanine (F). This is indicative of a consensus structure wherein the aromatic residues are important for the drug binding. The remaining sample of twenty-four isolates was distributed among seven different sequences in the ratio 9:6:5:3:1. All the peptides had a high hydrophobic index. A potentially cyclic sequence VCDW-WGWGIC (SEQ. ID. NO.: 3) had been detected in the isolate $V_6$.

EXAMPLE III

Specific Conformation

In order to characterize the binding of individual clones, four different clones $V_6$, $V_{10}$, $V_{12}$ and $A_4$ together with the control phage $X_1$ were analyzed for binding to doxorubicin in an ELISA experiment in which polyclonal anti-phage antibodies were used to detect bound phages. Antisera were raised against fd-Tet phage lacking insertion into pIII. Three rabbits were injected intramuscularly with 0.5 mg of fd-ted phages in Freunds complete adjuvant and then boosted three times with 0.25 mg of fd-ted phages in incomplete adjuvant at 3 weeks intervals. The titer of the antisera was measured with an ELISA using phage immobilized in Maxisorb microtiter wells as described (Motti et al., *Gene,* 146: 91–198 (1994)). All rabbits produced high titer antisera after the second boost. Sera collected after the third boost from one of the rabbits was used for the assays.

Figure 4:
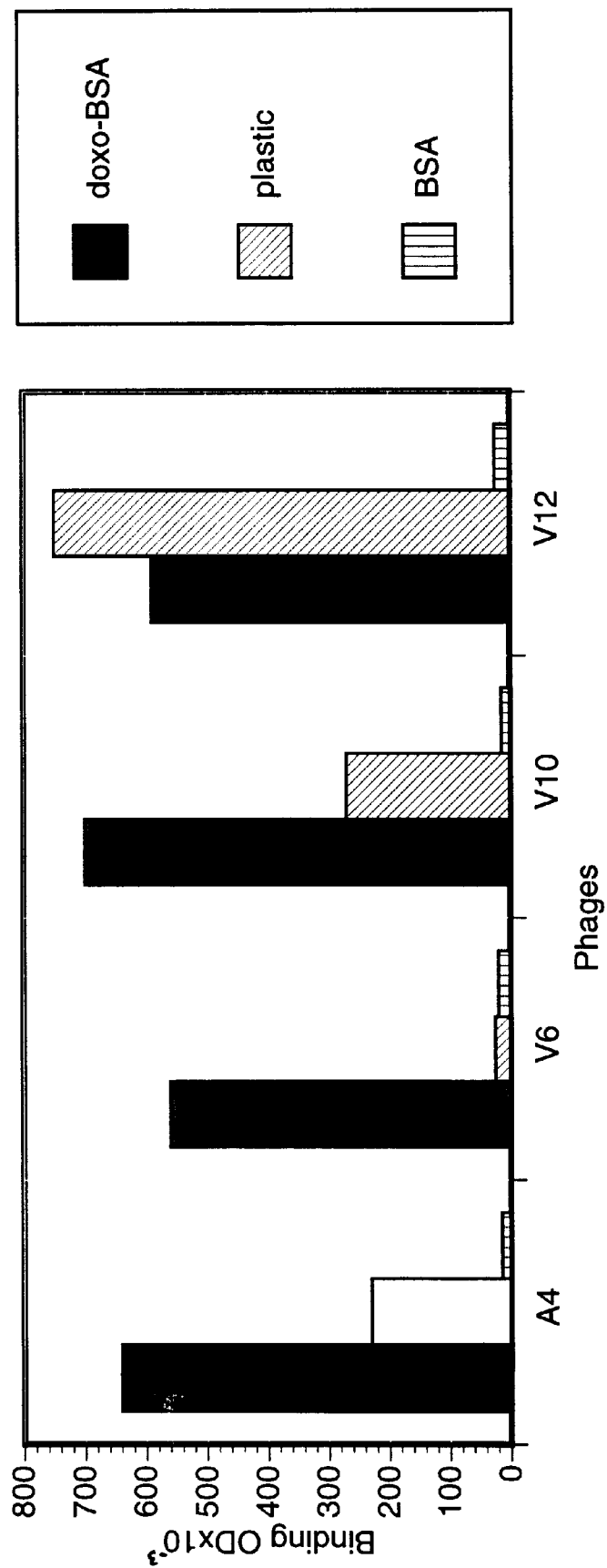
FIG. 4 illustrates the results of ELISAs for four different phages ($A_4$, $V_6$, $V_{10}$, $V_{12}$) with immobilized doxo-BSA on wells and labelled polyclonal anti-phage serum to detect bound phages.

Phages from the second PEG precipitation (Parmley & Smith, *Gene,* 73: 305–318 (1988)) were dissolved in 210 μl of 0.15 M NaCl, microfuged for 1 min, precipitated from 200 μl of the supernatant by the addition of 21.2 μl of 1 M acetic acid, and by incubation for 10 min at room temperature and 10 min on ice. (Scott & Smith, *Science,* 249: 386–390 (1990)). Phages were sedimented (microfuged, 45 min, 4 C.) and dissolved in 60 μl of TBS. Phage concentration was determined as described in Parmley & Smith, *Gene,* 73: 305–318 (1988). These partially purified phages were subjected to one round of screening, except that the phages were not acid eluted. Instead, blocking solution [250 μl of nonfat dry milk (50 μg/ml) in 0,05% TWEEN20 ™/TBS (TWEEN20 ™: Polysorbate 20)] was added to the wells. After a 2-h incubation at room temperature, wells were washed three times in 0.05% TWEEN20 ™/TBS. Rabbit anti-phage fd-ted serum, 100 μl of a 1:1000 dilution (in blocking solution) was added to wells and incubated overnight. Wells were washed seven times in 0.05% TWEEN20 ™/TBS and once with TBS; 100 μl of a peroxidase-conjugated goat anti-rabbit immunoglobulin were then added (Kirkegaard & Perry Labs, Maryland, USA, diluted 1:1000). After a 2-h incubation at room temperature, the wells were washed seven times with 0.05% TWEEN20 ™/TBS and once with TBS. To reveal the reaction, 100 μl of ABTS solution (Kirkegaard & Perry Labs, Maryland, USA) were added, incubated for 30 min at room temperature, and read in a microplate reader. Data are reported as $OD_{405}$ for sample wells minus the average blank. In each case, a significant binding of display phage to doxorubicin was observed (FIG. 4).

In practice, an important aspect of the use of peptides on phage display libraries is the characterization of individual phage isolates after sequential rounds of affinity purification. Isolated phages may bind to other components found on an immobilizing surface, or may bind to the protein target at sites other than the active site. In order to avoid the selection of plastic-binding phage (Adey et al., *Gene,* 156: 27–31 (1995)) we included, in our ELISA experiments, empty wells and wells containing only BSA as controls. None of the four isolated phages could bind to BSA. Phage $V_{12}$ showed strong binding to plastic, while phages $V_{10}$ and $A_4$ had moderate binding, and phage $V_6$ had only background binding to plastic. Accordingly, at least one of the isolated phages $V_6$, showed strong specific binding to doxorubicin itself.

EXAMPLE IV

Displacement Assay

In order to test the affinity of the peptide identified in the phage $V_6$, we used three different classes of cytotoxic MDR drugs: vinblastine, doxorubicin and verapamil, along with a non-MDR control drug, Ara-C. Phage $V_6$ ($10^{10}$ virions) was preincubated for 1 hr at room temperature in 100 μl of 0.1% BSA/PBS buffer containing different drug concentrations ($10^{-4}$ M to $10^{-9}$ M), and aliquots were added to microtiter wells, which were then coated with doxorubicin-BSA as previously described in Example II. After a 1-h incubation at room temperature, the wells were washed 12 times with PBS and the remaining bound phages eluted with 50 μl of 0.1 M HCl (pH adjusted to 2.2 with glycine). The phages were quantitated by titration on log phase of *E. coli* K91Kan cells plated on LB plates with 40 mg/ml tetracycline (Parmley & Smith, *Gene,* 73: 305–318 (1988)).

Figure 5:
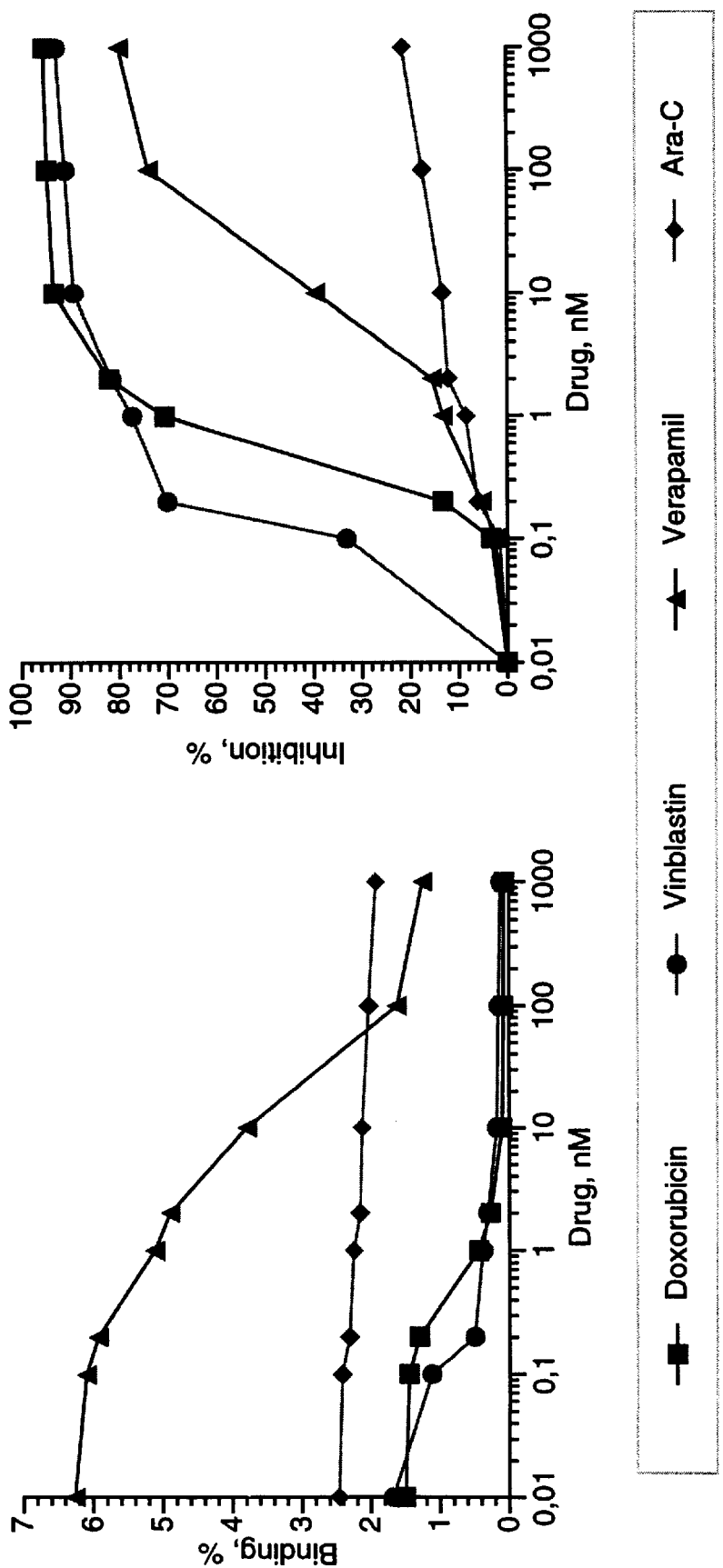
FIG. 5 illustrates the results of inhibition of $V_6$ phage binding to doxorubicin by different anticancer drugs.

Vinblastine proved to be three times more efficient than doxorubicin in inhibiting the binding of phages $V_6$ to doxorubicin as shown by the $IC_{50}$ values of $1.5 \times 10^{-9}$ M and $4.5 \times 10^{-9}$ M, respectively (FIG. 5). Verapamil was about 100 times less potent than vinblastine as shown by $IC_{50}$ value of $2 \times 10^{-7}$ M. In contrast, Ara-C was essentially inactive. The $IC_{50}$ derived for vinblastine, doxorubicin, and verapamil were in general agreement to the resistance profile mediated by Pgp with high resistance to vinca alkaloids (vinblastine), intermediate resistance to anthracyclins (doxorubicin) and low resistance to verapamil (Boer et al., *Proc. Amer. Ass. Cancer Res.,* 36: 331 (1995)).

Accordingly, using the phage displacement assay, the binding of the $V_6$ phage was shown to be specific for doxorubicin, and the interaction of the phage with doxorubicin could be blocked by three MDR-drugs: vinblastine, doxorubicin and verapamil.

Therefore, the peptide library has proven useful to determine a receptor site which behaves like the natural receptor with respect to the binding of MDR-drugs. It was difficult to obtain doxorubicin-binding clones using a circular library C—$X_{10}$—C (SEQ ID NO:26). In this particular case, the presence of the flanking cysteine residues may impose a configuration such that the peptides cannot adequately mimic the natural MDR-receptor site. This does not, however, exclude the possibility that another circular library with a different variable region length or a different complexity can be used. Indeed, the fact that the $V_6$ clone analyzed from a linear decapeptide library showed a potential circular peptide whose structure would be C—$X_7$—C (SEQ ID NO:21) is indicative that a library having exposed heptapeptides would be enriched in peptides mimicking the MDR-receptor site. The foregoing facts demonstrate that not all circular libraries of any length are capable of providing suitable peptides for any screening ligand. This is particularly true for constrained peptides.

Another approach to find properly displayed peptides binding any ligand is to first screen a linear enriched library of an adequate peptide length and to pick up clones of a high affinity by lowering the concentration of the screening ligand such that one or more peptides with a constrained conformation are retrieved and sequenced. The sequence then reveals where the cysteine residues are located in a constrained peptide. The suitable circular peptide library is then constructed in order to obtain a larger family of peptides. Otherwise, ligands having affinity for a particularly conformed peptide may be so capricious that a defined library would not be suitable to discover target peptides.

The $V_6$ peptide had been shown to be potentially cyclic and its structure is grossly C—$X_7$—C (SEQ ID NO:21). A cyclic heptapeptide library made in accordance with the above teachings will thus further aid in retrieving other peptides analogous to the $V_6$ peptide.

A short constrained peptide library has been described by O'Neil et al. (in *Proteins: Structure, Function and Genetics,* 14: 509–515 (1992)), which library had the structure C—$X_6$—C (SEQ ID NO:27). This library has been used to retrieve a peptide containing an RGD sequence binding to platelet glycoprotein IIb/IIIa. The discovered peptides contained the very short RGD or KGD sequence and even though the circular library was more enriched in binding clones than the corresponding linear library $X_6$, there is no indication that the peptides were representing a discontinuous peptide sequence because this type of sequence has a low level of complexity. In the present case, a discontinuous receptor sequence was obtained, bringing in proximity the aromatic residues involved in the drug binding.

This is therefore the first time that peptides mimicking a complex molecule having a discontinuous receptor site have been retrieved. The obtained peptides are useful for making MDR neutralizing antibodies, since they mimic the binding site of the natural MDR receptor. Alternatively, these peptides may be used as ligands themselves to reiterate the procedure in order to find doxorubicin analogs.

Figure 8:
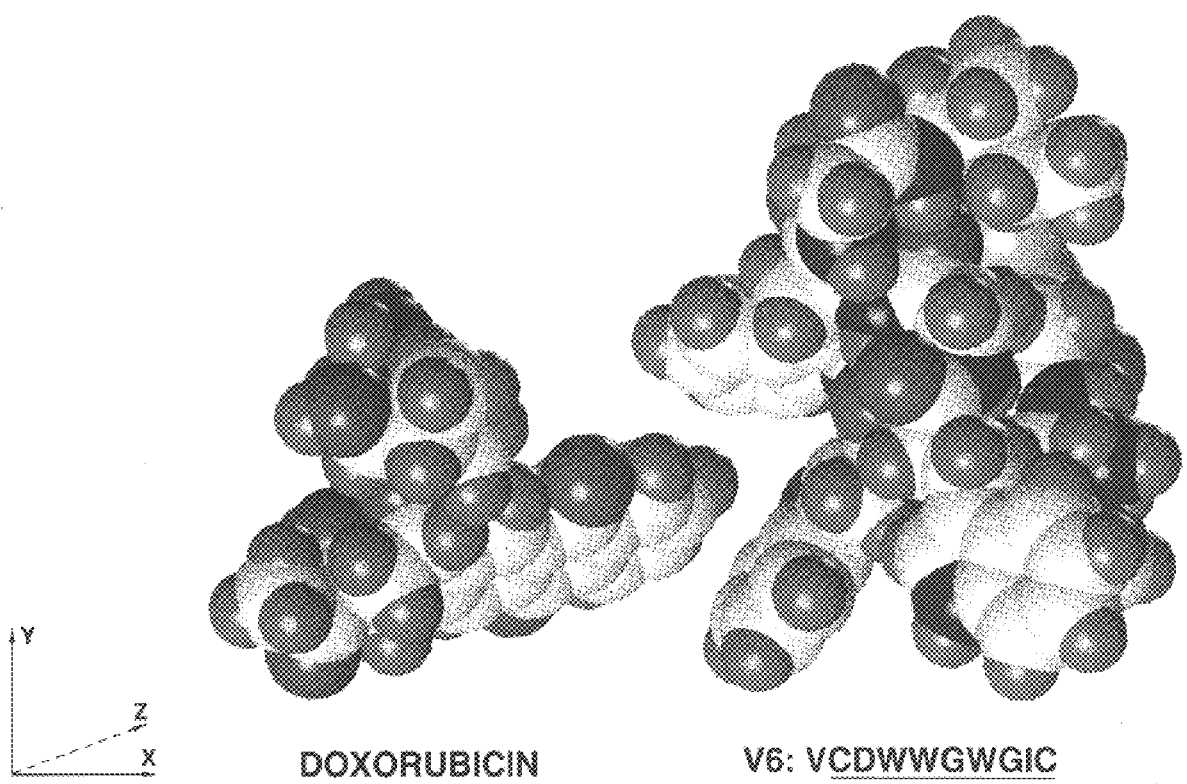
FIG. 8 depicts a structural model of the interaction between the peptide $V_6$ (SEQ ID NO:3) and doxorubicin.
Figure 9:
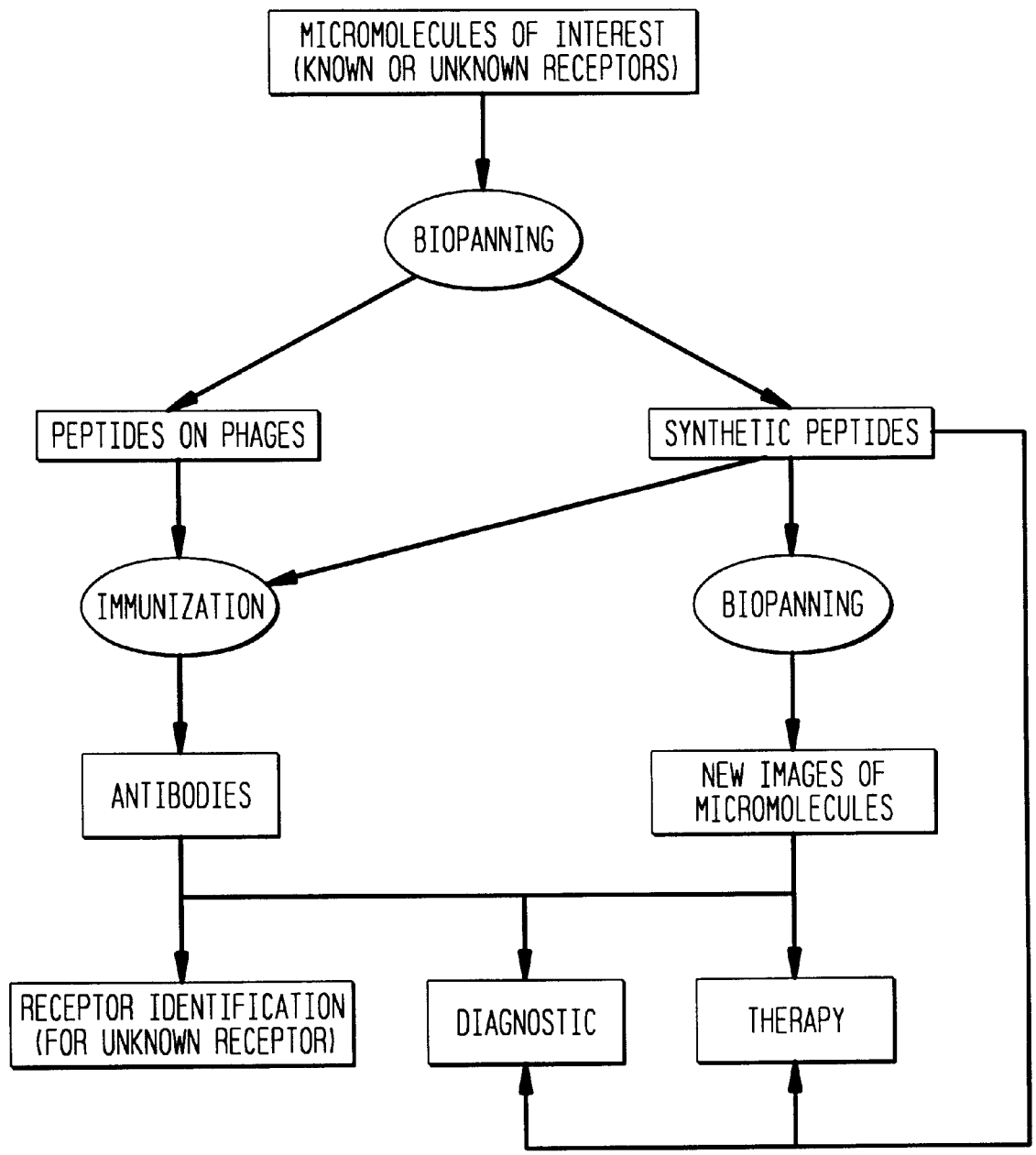
FIG. 9 is a schematic representation of the process and application of the present invention.

The effect of peptide-directed antibodies has been considered problematic for discontinuous epitopes (Felici et al., Gene, 128: 21–27 (1993)), since peptides mimicking discontinuous epitopes have not been able to elicit the production of antibodies recognizing the natural antigen. Structure modeling of established sequences using SIBYL Molecular Graphics (version 6.1a) indicates that all of these peptides, when represented in beta-turn conformation, contain a hydrophobic envelope formed by two tryptophan residues presented in the consensus motif (FIG. 7). Powell method with Tripos force field and Gasteiger-Huckel method for charge calculation were used for computations. The dielectric constant, E=80, was used for solvent simulation. Initially, energy minimization was carried out on the peptide alone. Then, after having achieved the energy gradient of 0.05 kCal, the drug molecule (doxorubicin) was docked as close to the tryptophan pocket as possible, and energy minimization was repeated again (FIG. 8).

The most important result from the experiments in molecular modeling was that doxorubicin, vinblastine and verapamil molecules could be easily docked between two indole rings of tryptophan residues. This produced a higher benefit (up to 20 kcal/mol) in Van der Walls energy, as compared to Ara-C-peptide complex. While originally oriented at the angle of 30 degrees in the starting peptide, the indole rings of tryptophan resides, upon complexing on either side of the drug molecule, became nearly parallel.

A molecular docking of the drug molecules used in this study into $V_6$-peptide structure followed by minimization of hypothetical complexes showed that doxorubicin, vinblastine and verapamil can easily be inserted into the cavity between two tryptophans.

In view of the foregoing, the $V_6$ peptide mimics the original MDR receptor site to elicit the production of antibodies against the natural receptor. Therefore the $V_6$ peptide and related peptides would be useful as immunogens as well as a second screening ligands to obtain two types of effector molecules: antibodies and doxorubicin analog peptides, respectively.

EXAMPLE V

Circular Peptide Libraries Having Conserved Disulfide Frameworks

A circular peptide library was prepared by synthesizing oligonucleotides containing degenerate codons of NNK (or NNB) motif. Here N is equimolar A, C, G, or T and K is equimolar G or T (B=G, T or C). This motif codes for all twenty amino acids at each locus in the hypervariable regions (alternatively, the degenerate portion can be assembled by the condensation of twenty activated trinucleotides, one for each amino acid). Two to six cysteine codons are preserved to produce the characteristic frameworks and n varies for 1 to 20 in each unit separately ($n_1$, $n_2$, $n_3$, or $n_4$):

1-loop Cys(NNK)$_n$Cys (SEQ ID NO:16 )

2-loop CysCys (NNK)$_{n1}$Cys(NNK)$_{n2}$Cys alpha (SEQ ID NO:17)

3-loop CysCys(NNK)$_{n1}$Cys(NNK)$_{n2}$Cys(NNK)$_{n3}$CysCys mu (SEQ ID NO:18)

4-loop Cys(NNK)$_{n1}$Cys(NNK)$_{n2}$CysCys(NNK)$_{n3}$Cys (NNK)$_{n4}$Cys omega (SEQ ID NO:28)

Figure 6:
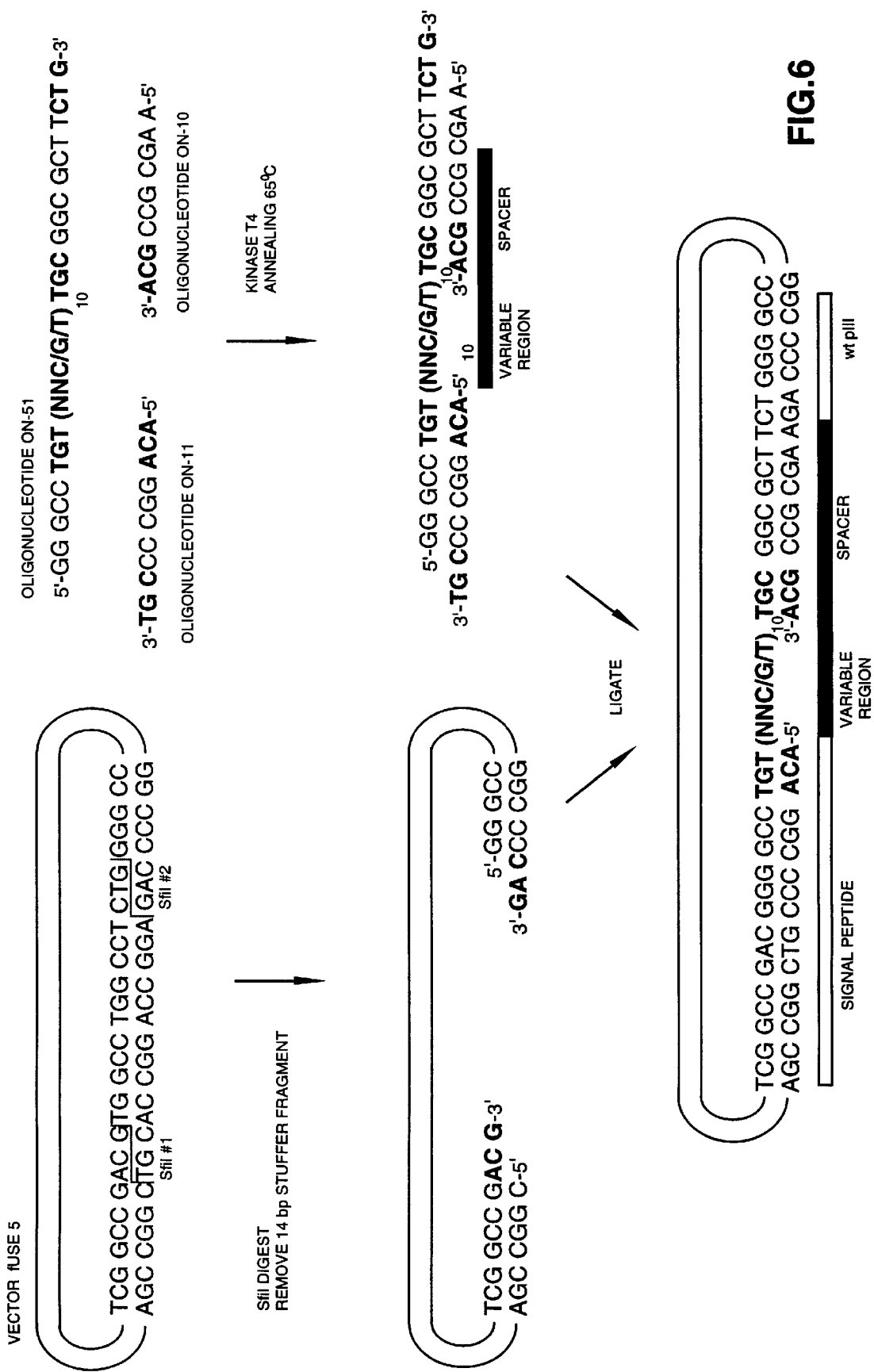
FIG. 6 (SEQ ID NOs:29, 31–32, and 34–37) depicts the conotoxin peptide library construction. The oligonucleotide ON-51 (SEQ ID NO:34) was annealed to two "half-site" fragments ON-11 (SEQ ID NO:35) and ON-10 (SEQ ID NO:36) to form cohesive termini complementary to SfiI sites in the vector.

A pair of cysteine that flank a string of variable residues results in the display of the variable residues in a loop closed by a disulfide bond, as discussed above. Oligonucleotides which were cloned to produce 1-loop peptide library, have the general structure shown in FIG. 6. The 5' and 3' ends have a fixed sequence, chosen to reconstruct the amino acid sequence in the vicinity of the signal peptidase site. The central portion contained the variable regions which comprise the oligonucleotide library members, and also codes for spacer residues on either one or both sides of the variable sequence. A collection of oligonucleotides encoding all possible decapeptides was synthesized with the sequence 5'-GGGCC{TGT(NNB)$_{10}$TGC}GGCGCTCTG-3' (SEQ. ID. NO.: 12); where N was A, G, T and C (nominally equimolar), B was G, T and C (nominally equimolar), and three nucleotides TGT (or TGC) code for cysteine. This sequence, designated ON-51, was ligated into two Sfil sites of the fUSE5 vector after annealing to two "half-site" oligonucleotides, ON-11 (5'-ACAGGCCCCGT-3'; SEQ. ID. NO.: 13) and ON-10 (5'-AAGGGCCGCA-3'; SEQ ID NO.: 14), which are complementary to the 5' and 3' portions of ON-51, respectively. "Half-site" oligonucleotides anneal to the 5' - and 3' -ends of oligonucleotide ON-51 to form appropriate Sfil cohesive ends. This left the appropriate Sfil site exposed without the need to digest with BgII, thus avoiding the cutting of any BgII sites that might have appeared in the variable region. The vector fUSE (100 μg) was digested to completion with Sfil, and ethanol precipitated twice in the presence of 2 M ammonium acetate. Oligonucleotides were phosphorylated with T4 kinase, and annealed by heating at 65 C. for 5 min in 20 mM Tris-HCl, pH 7.5, 2 mM MgCl$_2$, 50 mM NaCl, by mixing 1.5 μg ON-11, 1.2 μg ON-10 and 0.5 μg ON-51 with 20 μg Sfil-digested fUSE RF DNA. The mixture was allowed to cool slowly to room temperature. This represented an approximate molar ratio of 1:5:100:100 (fUSE5 vector:ON-51:ON-11:ON-10). The annealed structure was then ligated to Sfil-cut fUSE5 RF DNA to produce a double-stranded circular molecule with a small, single stranded gap. These molecules were transformed into host cells under conditions described in Example 1.

To sample additional diversity in the peptide libraries, the number of residues between the half cysteines was varied. This was accomplished as follows:

1) Five separate oligonucleotide synthesis columns were prepared with the first nucleotide immobilized on resin;
2) The common regions of the 3' end of the oligonucleotides were synthesized (all columns go through the same cycles to produce the cloning site, etc., on this end). Synthesis on all column was carried out through the first Cys (or CysCys) of the framework.
3) On column 1, two degenerate codons were synthesized; on column 2, three degenerate codons are synthesized and so on. Each column now had oligonucleotides with either 6, 7, 8, 9 or 10 degenerate codons in the first hypervariable regions;

4) One Cys codon was now added to all columns (this is the second Cys of the omega class or the third Cys of the mu class);

5) The resins from all five columns were removed, mixed well, and reallocated among the five columns. Each column now contains oligonucleotides with all five lengths of the first hypervariable region;

6) Each column was again put through either 6, 7, 8, 9, or 10 cycles of degenerate codon synthesis as before; and the next Cys codon (or CysCys for omega) was added;

7) The resins were again removed, mixed and redistributed to the five columns, and the process was repeated through three (for mu) or four (for omega) hypervariable regions;

8) The common sequence on the 5' end of all the oligonucleotides was synthesized, and the oligonucleotides were removed from resins and purified as previously described.

Folding of the peptides to achieve biological activity may be directed by a forty amino acid conserved "leader peptide" at the N-terminus of the pre-toxin molecule. Synthesized as part of a recombinant fusion protein, this leader may enhance the folding of many of the members of the library into the "correct" like framework. Alternatively, allowing the cysteine framework to form in a random manner produces a variety of structures, only some of which mimic the framework. This collection provides additional multi-loop structures that add to the diversity of the peptide library.

In order to minimize the possibility that one conformation would predominate, a gentle reduction to the phage in vitro was used, followed by mild oxidation to form most of the conformations. Mild reduction/oxidation is accomplished by treatment with 0.2 to 5 mM DTT followed by extensive dialysis to non-reducing conditions. A regenerable, immobilized lipoic acid column to rapidly pass the peptide-bearing particles over can also be used.

This general format for using the secondary framework structure of conotoxins can also be applied to other peptide families with biological activities as a basis for designing and constructing peptide expression-screening libraries in accordance with the present invention.

The identification of the doxorubicin binding $V_6$ clone shows that at least a one loop C—$X_7$—C (SEQ ID NO:21) library is useful in identifying doxorubicin binding peptides.

EXAMPLE VI

Synthesis of peptide derivatives $V_6$ analogs or derivatives thereof are synthesized wherein one of the tryptophan residues are substituted to ease the chemical synthesis. The residues present in the peptide derivatives are substituted in an empirical fashion (classically called a structure-function study). The first step is to substitute at least one of the tryptophan conserved amino acids and each other amino acid and verify the binding affinity to doxorubicin and other MDR drugs. After obtaining a good binding affinity for a selected peptide, its antagonist or agonist properties on the natural receptor is verified, in an artificial receptor system or in vivo. The DNA insert from the recombinant phage is excised and reintroduced in an expression vector to produce the $V_6$ peptide or any related peptide by a recombinant technology. Alternatively, the pIII protein is excised at the end of the bacteriophage and the peptide purified by HPLC.

The structure of a peptide is optimized to increase its affinity and to use crystallography to design and understand the topology of a peptide.

Although the foregoing invention has been described in details by way of illustrations and examples for purpose of clarity and of understanding, it will be apparent that certain changes and modifications may be practiced without departing from the teachings of this invention, and these changes and modifications are within the scope of the appended claims.

What is claimed is:

1. An oligopeptide having the formula:

$(X)n—W/F—X—X—W/F—(X)n_1$ wherein each X is the same or different amino acid,
W/F is trypotophan or phenylalanine, and
each of n and $n_1$ is the same or different integer having a value of 2 to 20.

2. An oligopeptide as defined in claim 1, wherein $(X)n$ is $(X)n\text{-}2$—C—X—, $(X)n_1$ is —X—X—C—$(X)n_1\text{-}3$, wherein $n_1\text{-}3$ is at least one, and
C is cysteine.

3. An oligopeptide as defined in claim 1, wherein W/F is trypotophan.

4. A nucleic acid encoding an oligopeptide according to claim 1.

5. A nucleic acid encoding an oligopeptide according to claim 2.

6. A recombinant vector comprising the nucleic acid of claim 4.

7. A recombinant vector comprising the nucleic acid of claim 5.

8. A recombinant vector according to claim 6; which comprises an expression vector.

9. A recombinant vector according to claim 7; which comprises an expression vector.

10. A bacterial host comprising the vector of claim 6.
11. A bacterial host comprising the vector of claim 7.
12. A bacterial host comprising the vector of claim 8.
13. A bacterial host comprising the vector of claim 9.

* * * * *